United States Patent [19]

Matthews

[11] Patent Number: 5,016,620

[45] Date of Patent: May 21, 1991

[54] SPLINE AND SPLINTING BOARD COMBINATION

[75] Inventor: Max Matthews, Auburn Hills, Mich.

[73] Assignee: Medical Concepts, Inc., Rochester Hills, Mich.

[21] Appl. No.: 460,692

[22] Filed: Jan. 4, 1990

[51] Int. Cl.⁵ .................................. A61F 5/01
[52] U.S. Cl. ............................ 128/78; 128/870; 128/87 B
[58] Field of Search ............ 128/847, 870, 876, 87 R, 128/121.1, 124.1, 84 C, 87 B, 69, DIG. 20, DIG. 23, 78; 5/82 R

[56] References Cited

U.S. PATENT DOCUMENTS

| | | | |
|---|---|---|---|
| 2,521,530 | 9/1950 | McGuffage | 128/DIG. 20 X |
| 3,707,734 | 1/1973 | Matthews | 5/82 |
| 3,737,923 | 6/1973 | Prolo | 128/870 X |
| 4,340,042 | 7/1982 | Smith | 128/87 R |
| 4,789,202 | 12/1988 | Alter | 128/78 X |

OTHER PUBLICATIONS

Maryland Institute for EMS Systems, *The Maryland Way EMT-A Skius Manual*, Baltimore, 1986, pp. 5-1-3-5-20, 5-25-5-31.

J. of Bone & Joint Surgery, Jul. 1955, vol. 37-A, #4, Advertisement, p. 53.

*Primary Examiner*—Robert A. Hafer
*Assistant Examiner*—Kevin G. Rooney
*Attorney, Agent, or Firm*—Dykema Gossett

[57] ABSTRACT

A spline and splinting board combination is disclosed that comprises a two-part board structure with an upper board and a lower board that may be adjustably secured to each other. The upper board may be utilized independently when a small child or infant is to be transported and has a pair of belt receiving slots that allows the board to be utilized with differing heights of small children or infants. The upper board is adjustably secured to the lower board through a pair of thumb screws received in adjustment slots to allow adjustment of the distance from the top of the upper board to the bottom of the lower board to correspond to a desired distance for a particular patient. Inflatable cervical and lumbar supports are disclosed that may be quickly inflated or deflated to provide additional supports to those areas of the patient.

9 Claims, 4 Drawing Sheets

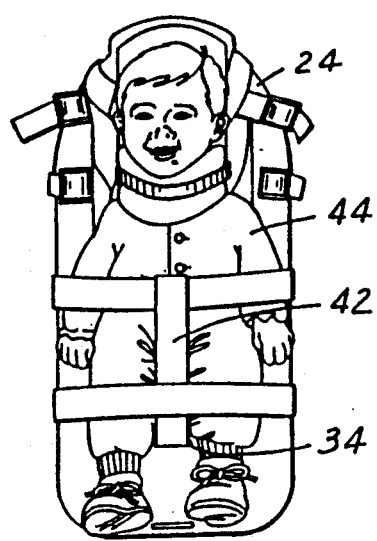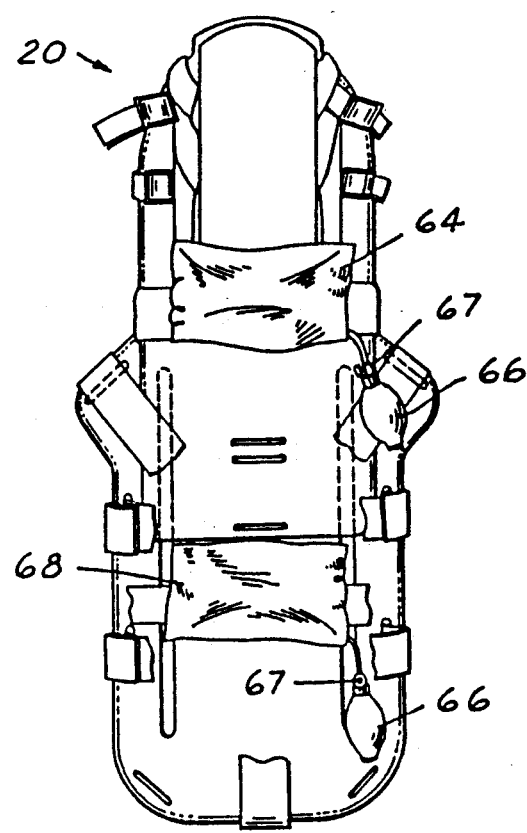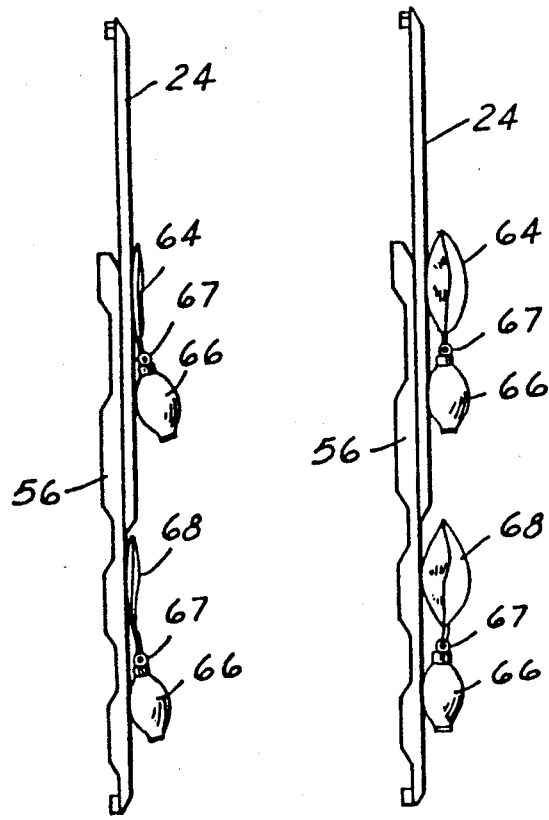
FIG.3
FIG.7B FIG.7C FIG.7A

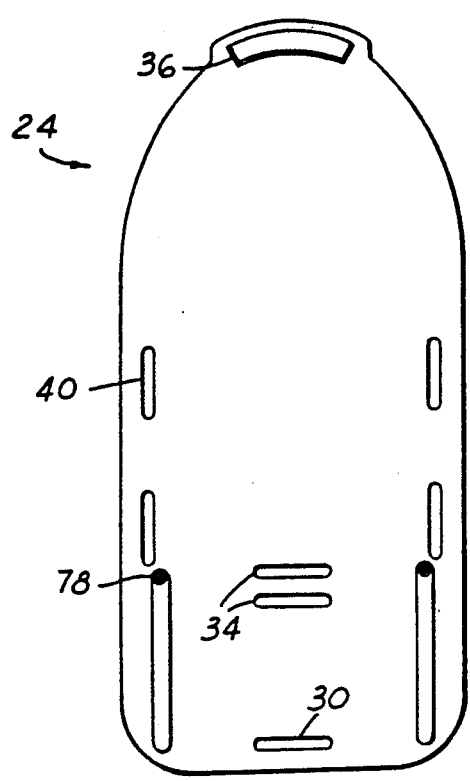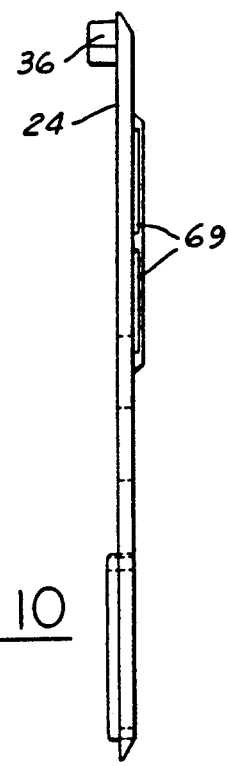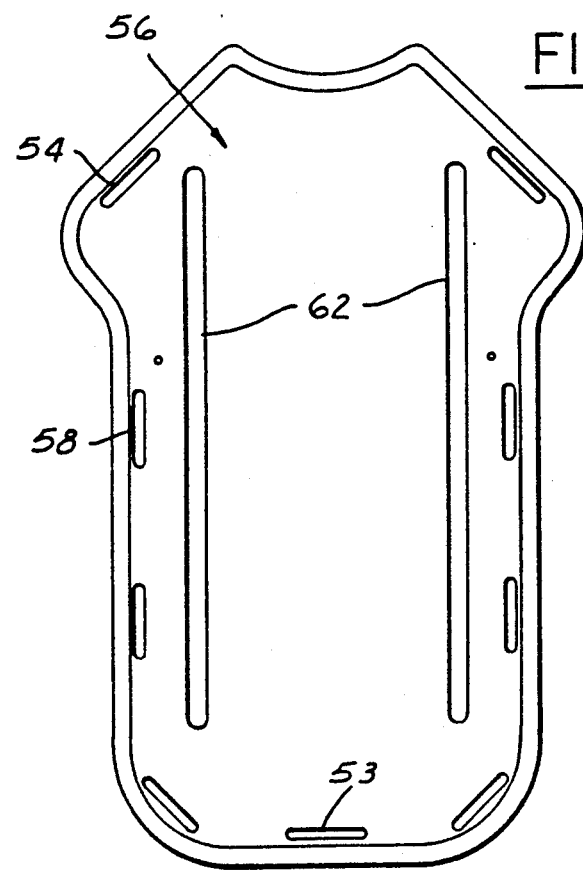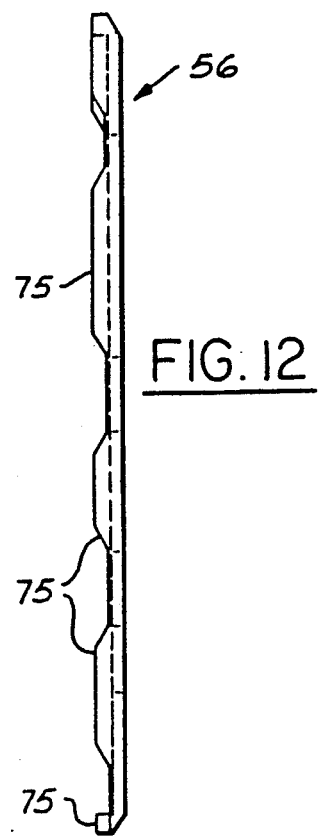

SPLINE AND SPLINTING BOARD COMBINATION

BACKGROUND OF THE INVENTION

This application relates to an improved spline and splinting board that can be readily adjusted for use with injured patients of any height. More particularly, this invention relates to a spline and splinting board combination that includes two boards, only one of which need be used, and the combination of which can be adjusted to conform to various sizes of patients.

A prior art splinting board is illustrated in U.S. Pat. No. 3,707,734, issued to the inventor of the present application and includes a two board structure that can be utilized with only a single board if only the upper portion of the patient need be immobilized. This device immobilized a patient during transport after receiving an injury to the spine or neck. It is important that a board used for this purpose conform to the individual characteristics of the particular patient, support and securely retain the patient's head and spinal area during transport.

It is, of course, impractical to have a plurality of spline and splinting boards of various sizes transported within an ambulance and thus it is desirable to have spline and splinting boards be as adjustable as possible to conform to the various height patients that may be encountered. The spline and splinting board disclosed in the above-mentioned patent, while having desirable features, is insufficient in some regards since it may not be readily adjustable to conform to various heights of patients.

It is an object of the present invention to disclose a spline and splinting board combination in which the overall length can be adjustable to conform to the individual characteristics of a particular patient or to be more readily received with a compact automobile, or other confined space.

It is further an object of the present invention to disclose a spline and splinting board combination that is utilized in combination with inflatable cervical and lumbar supports to provide proper support to a patient being transported upon the spline and splinting board combination.

SUMMARY OF THE INVENTION

The present invention discloses a spline and splinting board combination which employs an upper board secured to a lower board at adjustable positions to vary the distance from the top of the upper board to the bottom of the lower board. The distance from the top of the upper board to the bottom of the lower board defines an overall length of support provided by the board. The upper board may be utilized by itself when a small child or infant is to be supported on the board. Belts secure the patient to the boards and the upper board has two distinct belt-receiving slots to accommodate differing heights in small children or infants.

In a preferred embodiment of the present invention, the upper board includes a belt receiving slot near its vertically lowermost portion that receives a belt when a small child is to be supported on the board and has additional belt slots received vertically upwardly from this lowermost slot to provide belt slots for an infant to be supported on the board. The upper board also has thumb screw apertures that receive thumb screws. Both the thumb screw apertures and the thumb screws pass through elongate adjustment slots on the lower board. The thumb screw apertures slide within the adjustment slots to guide the upper board on the lower board. The thumb screws are tightened through the adjustment slots on the lower board into the thumb screw apertures to secure the lower board at any of a plurality of positions with respect to the upper board.

In a most preferred embodiment of the present invention, inflatable cervical and lumbar supports are placed upon the boards to provide support to the patient during transport. These inflatable supports are preferably inflated by an air bulb and have an air release valve adjacent to the bulb.

These and other objects and features of the present invention will be best understood from the following specification and drawings of which the following is a brief description.

BRIEF DESCRIPTION OF THE DRAWINGS

FIG. 3 is a front view of the spline and splinting board combination utilized with an infant.

FIG. 7A is a view similar to FIG. 6 showing the cervical and lumbar supports of the present invention.

FIGS. 7B and 7C are cross-sectional views through the device illustrated in FIG. 7A.

FIG. 9 is a rear view of an upper board of the spline and splinting board combination of the present invention.

FIG. 10 is a side view of the upper board illustrated in FIG. 9.

FIG. 11 is a rear view showing the lower board of the spline and splinting board combination of the present invention.

FIG. 12 is a side view showing the lower board illustrated in FIG. 11.

DETAILED DESCRIPTION OF A PREFERRED EMBODIMENT

Figure 1:
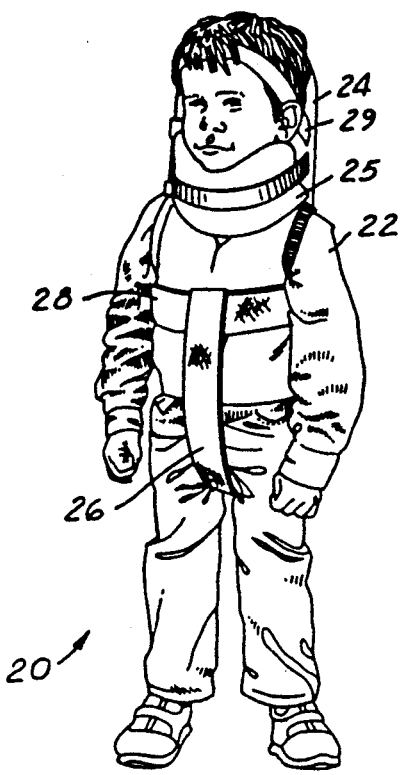
FIG. 1 is a front view of the spline and splinting board combination utilized with a small child.

A spline and splinting board combination 20 according to the present invention is illustrated in FIG. 1 supporting a small child 22 upon upper board 24. Neck brace 25 is secured to upper board 24 and retains the patient's neck in a static position with respect to board 24. Belt 26 and cross belt 28 secure child 22 to board 24. Head brace 29 secures the child's head to board 24.

Figure 2:
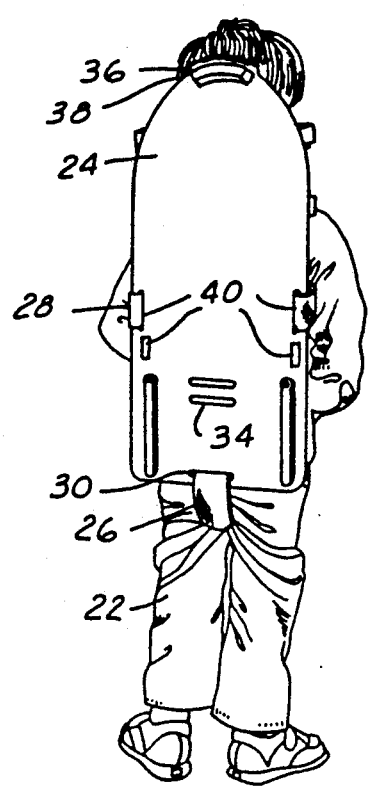
FIG. 2 is a rear view of the spline and splinting board combination utilized with a small child.

As shown in FIG. 2, slot 30 receives belt 26 while slots 40 receive belt 28. Slots 34 are spaced vertically upwardly from slot 30.

Handle portion 36 extends rearwardly from upper board 24 and head portion 38 of upper board 34 has a smaller lateral dimension than the remainder of upper board 24. Additional slots 40 are shown on each lateral side of upper board 24.

As shown in FIG. 3, upper board 24 can be utilized with belts 42 passing through slots 34 to secure an infant 44 to the board. Depending on the height of the particular patient, medical personnel determine whether the particular child is better supported by belts passing through slots 34 or belts passing through slot 30.

Figure 4A:
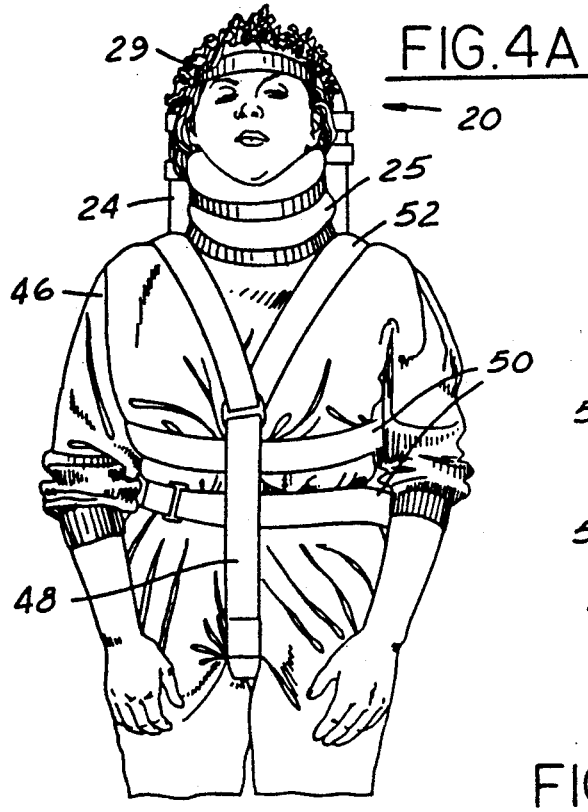
FIG. 4A is a front view of the spline and splinting board combination utilized with an adult.

As shown in FIG. 4A, an adult 46 is secured through belts 48, cross belts 50, and shoulder belts 52 to spline and splinting board combination 20.

Figure 4B:
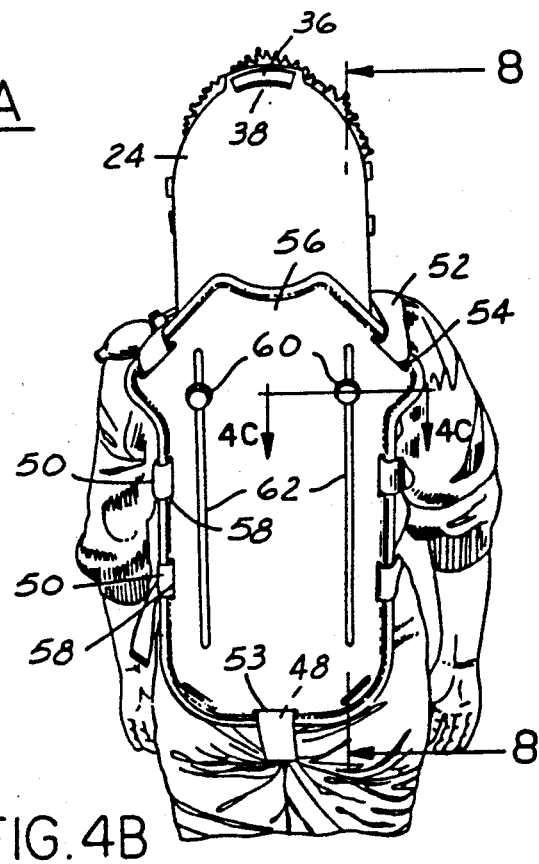
FIG. 4B is a rear view of the spline and splinting board combination utilized with an adult.

As shown in FIG. 4B, slots 54 are formed within lower board 56 to receive belt 52. Slots 58 receive belts 50 and slot 53 receives belt 48. Thumb screws 60 extend through adjustment slots 62 in lower board 56 to secure lower board 56 to upper board 24 in a manner that will be explained below.

Figure 4C:
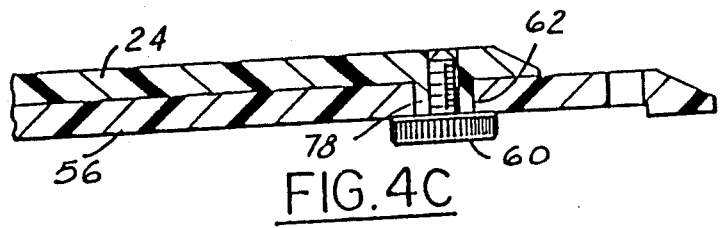
FIG. 4C is a cross-sectional view along line C—C as illustrated in FIG. 4B.

FIG. 4C is a cross-sectional view along line C—C illustrated in FIG. 4B and shows upper board 24 connected to lower board 56 with thumb screw aperture 78 extending through adjustment slot 62. Thumb screw 60 also extends through adjustment slot and is received within thumb screw aperture 78. Thumb screw aperture 78 slides within adjustment slot 62 and guides upper board 24 as it is moved with respect to lower board 56. By tightening thumb screw 60 within thumb screw aperture 78 upper board 24 is secured to lower board 56 at a desired position.

Figure 5:
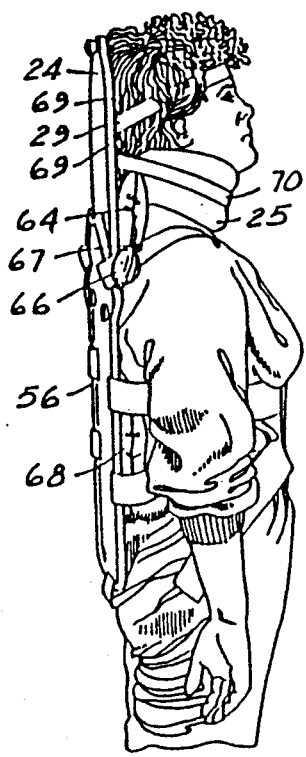
FIG. 5 is a side view of the spline and splinting board combination illustrated in FIG. 4B.

As shown in FIG. 5, cervical support 64 includes an air bulb 66 and vent valve 67 to control inflation and deflation. Cervical support 64 provides a cushioned support to the cervical area of patient 46. Lumbar support 68, which is similar to cervical support 64, is attached to support the lumbar area of patient 46. Slots 69 within upper board 24 receive head brace 29 and belt 70 associated with neck brace 25.

Supports 64 and 68 may also be utilized with infants or children. Since supports 64 and 68 must be accurately positioned relative to a patient to provide proper support, it is particularly important that they be used in combination with an adjustable board.

Figure 6:
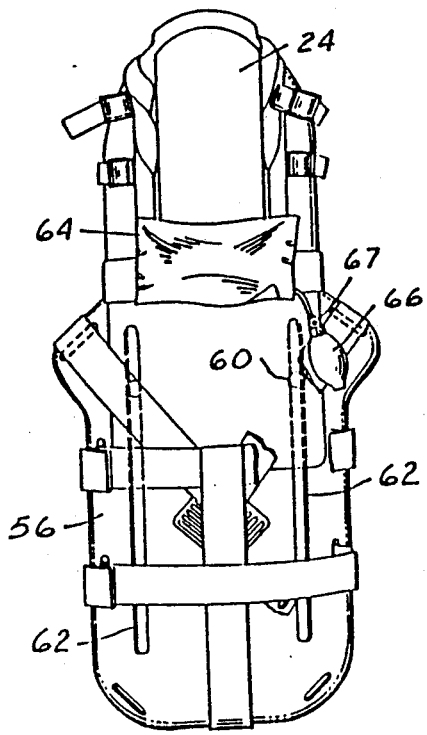
FIG. 6 is a front view of the spline and splinting board combination.

As shown in FIG. 6, upper board 24 is secured to lower board 56 through thumb screws 60 and cervical support 64 is received upon upper board 24.

FIG. 7A is a front view of spline and splinting board combination 20 having cervical support 64 mounted at an upper portion with air bulb 66 and vent valve 67 to provide inflation and deflation. Lumbar support 68 is mounted at a lower portion and also includes air bulb 66 and vent valve 67. Alternatively, a single bulb could be utilized on both supports 64 and 68 in combination with a quick connect/disconnect coupling. Also, it is envisioned that a single bulb could be connected through a tee-connector to both supports 64 and 68. The inflation and deflation would still be independently controllable through vent valves 67.

FIG. 7B is a cross-section through FIG. 7A and illustrates cervical support 64 and lumbar support 68 both being deflated. The patient would most preferably be initially supported upon the spline and splinting board combination 20 while supports 64 and 68 are deflated. Once the patient is secured to the spline and splinting board combination 20, air bulbs 66 are utilized to inflate supports 64 and 68 to provide support to the patient.

As shown in FIG. 7C, supports 64 and 68 have been inflated. When it is desired to deflate supports 64 and 68 vent valves 67 are opened and air escapes from the supports 64 and 68.

Figure 8:
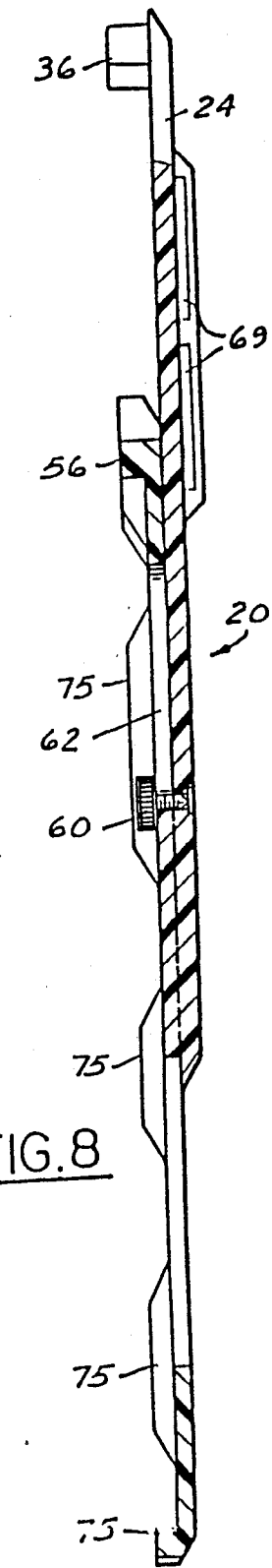
FIG. 8 is a cross section along line 8—8 as illustrated in FIG. 4B.

FIG. 8 is a cross-sectional view along lines 8—8 illustrated in FIG. 4B. Upper board 24 has handle 36 and slots 69 extending forwardly. Thumb screws 60 passes through adjustment slots 62 formed in lower board 56 and allows the adjustment of the distance between the top of upper board 24 and the bottom of lower board 56 such that the spline and splinting board combination 20 can be adjusted to conform to various heights of adult patients. Supports 75 extend rearwardly from lower board 56 to aid in transport.

FIG. 9 is a front view showing details of upper board 24 including handle 36, slots 40, slots 30 and 34 and thumb screw aperture 78.

As shown in detail in FIG. 10, handle 36 extends rearwardly from upper board member 24 while slots 69 extend forwardly. By having slots 69 spaced on each lateral side of upper board 24 and receiving belts for head brace 29 and neck brace 70 it is ensured that the head and neck of a patient will be securely retained in a fixed position relative to upper board 24.

As shown in FIG. 11, lower board 56 includes slots 54, 53 and 58. Adjustment slots 62 receive thumb screws 60.

FIG. 12 is a side view showing the details of lower board 56. Supports 75 extend rearwardly from lower board 56.

The operation of spline and splinting board 20 will now be explained with reference to the figures. When medical personnel encounter an injured patient, they first make the determination whether only upper board 24 is necessary or whether the combination of upper board 24 and lower board 56 will be utilized.

If a small child is to be supported upon spline and splinting board combination 20, only upper board 24 will normally be utilized. Belt slot 30 and belts 26 and 28 will be utilized to secure the small child to upper board 24. If an infant is encountered it may be preferable to utilize slots 34 in combination with slots 40 to secure the infant to board 24.

When a relatively taller patient is encountered, the combination of upper board 24 and lower board 56 is utilized and the distance between the top of upper board 24 and the bottom of lower board 56 is adjusted by releasing thumb screws 60 and moving upper board 24 relative to lower board 56. When upper board 24 has been moved relative to lower board 56 such that the distance is as desired for a particular patient, thumb screws 60 are tightened within thumb screw apertures 78 and lower board 56 is secured to upper board 24. Cervical support 64 and lumbar support 68 are initially deflated. Once the patient is secured, supports 64 and 68 may be inflated to provide additional support to the patient at these critical areas.

A preferred embodiment of the present invention has been disclosed, however, certain modification would be obvious to one of ordinary skill in the art and thus the following claims should be considered in order to determine the true scope and content of the present invention.

I claim:

1. A spline and splinting board combination that is adjustable to accommodate various size patients comprising:
   an upper board;
   a lower board;
   means for adjustably connecting said upper and lower board such that the distance between the top of said upper board and the bottom of said lower board may be adjusted to accommodate various size patients:

said upper board member being usable by itself to support patients of relatively lesser height;

belts to secure a patient to said upper board, and said upper board having belt slots to receive said belts;

said upper board has two groups of said belt slots, one of said groups being spaced vertically above the other of said groups to provide a choice of belt slots to accommodate various size patients;

said means for adjustably connecting said upper and lower boards comprises a pair of adjustment slots passing through one of said upper and lower boards and a pair of thumb screws received in the other of said upper and lower boards, said thumb screw passing through said adjustment slots and adjustably connecting said upper and lower boards;

two air cushion support members with one positioned to correspond to the cervical area of a patient and a second positioned to correspond to the lumber area of the patient;

each of said support members have a vent valve and a bulb at one lateral side to provide inflation and deflation of said support members; and said upper board member having a handle portion extending rearwardly near a vertically uppermost position and head and neck belt slots extending forwardly near a vertically uppermost position, said head and neck belt slots receiving belts to secure the head and neck of a patient.

2. A spline and splinting board as recited in claim 1, wherein said means for adjustably connecting said upper and lower boards comprises a pair of adjustment slots passing through one of said upper and lower boards and a pair of thumb screws received in the other of said upper and lower boards, said thumb screw passing through said adjustment slots and adjustably connecting said upper and lower boards.

3. A spline and splinting board combination as recited in claim 2, wherein said adjustment slots are formed through said lower board and said thumb screws are received in thumb screws apertures in said upper board, said thumb screw apertures extending into said adjustment slots to guide said upper board on said lower board.

4. A spline and splinting board combination as recited in claim 1, wherein at least one air cushion support member is provided upon the spline and splinting board combination to provide additional support to a patient.

5. A spline and splinting board combination as recited in claim 4, wherein there are provided two of said support members, one positioned to correspond to the cervical area of a patient and a second position to correspond to the lumbar area of a patient.

6. A spline and splinting board combination as recited in claim 5, wherein each of said supports have a vent valve and a bulb at one lateral side to provide inflation and deflation.

7. A spline and splinting board combination as recited in claim 1, wherein said upper board has a handle portion extending rearwardly at a vertically upper most position, and said lower board has supports extending rearwardly.

8. A method of supporting a patient having an individual height during transport upon a spline and splinting board combination which includes an upper board, a lower board and means for adjustably connecting the upper board member to the lower board including the steps of:

A. identifying a height limit below which a patient will be supported by the upper board alone, and above which the combination of the upper and lower boards are used;

B. identifying the relative height of a patient to be supported;

C. and if the height is below the predetermined height limit, as when the patient is an infant or child, utilizing only upper board, selecting one of a pair of vertically spaced belt slots to accommodate various heights of patients and securing the patient to the upper board by belts received in the selected slot;

D. and if the height is above the predetermined limit, as when the patient is an adult, using the combination of the upper and lower board adjustably securing the upper board with respect to the lower board such that the distance from the top of the upper board from to the bottom of the lower board corresponds to a desired distance for the individual patient and securing the patient to the board through belts.

9. A method as recited to claim 8, wherein cervical and lumbar inflatable air supports are provided.

* * * * *